United States Patent [19]

Sapoff

[11] Patent Number: 4,701,101
[45] Date of Patent: Oct. 20, 1987

[54] MODULAR MULTI-TUBE CATALYST LOADING FUNNEL

[75] Inventor: Paul C. Sapoff, Louisville, Ky.

[73] Assignee: Catalyst Technology, Inc., Buckner, Ky.

[21] Appl. No.: 789,753

[22] Filed: Oct. 21, 1985

Related U.S. Application Data

[62] Division of Ser. No. 588,985, Mar. 13, 1984, abandoned.

[51] Int. Cl.⁴ .............................................. B01J 4/00
[52] U.S. Cl. .................................. 414/786; 222/229; 414/162; 422/219
[58] Field of Search .................... 414/266–269, 414/162–164, 167, 183, 458, 403, 786; 422/219, 232, 197, 312; 222/241, 242, 411, 229, 547, 564; 141/331, 392

[56] References Cited

U.S. PATENT DOCUMENTS

| | | | |
|---|---|---|---|
| 3,094,245 | 6/1963 | Mizuno | 222/547 |
| 3,223,490 | 12/1965 | Sacken et al. | 422/219 |
| 3,314,557 | 4/1967 | Sackett, Sr. | 414/269 |
| 3,658,212 | 4/1972 | Ullberg | 222/241 X |
| 3,754,855 | 8/1973 | Siemssen et al. | 414/162 X |
| 3,887,209 | 6/1975 | Blanc | 414/458 X |
| 4,174,054 | 11/1979 | Hubbard | 222/241 |
| 4,402,643 | 9/1983 | Lytton et al. | 414/160 |
| 4,426,018 | 1/1984 | Ward | 222/411 X |
| 4,458,734 | 7/1984 | Scholle et al. | 422/219 X |

Primary Examiner—Robert J. Spar
Assistant Examiner—David A. Bucci
Attorney, Agent, or Firm—William R. Price

[57] ABSTRACT

A modular multi-tube catalyst loading funnel comprises a series of funnel modules, each equipped with a rotatable stirring rod, an opening at the bottom, and a variable-speed drive. With the apparatus, it is possible to control the drop rate of catalyst pellets in each of the funnels, by adjusting the speed of rotation of the metering rods. If more control is required, the metering rods may be raised or lowered in each funnel module to increase or decrease the speed of catalyst drop. Additionally, it is possible to utilize metering rods with various end configurations to alter the speed of the catalyst drop in the multitube catalytic reactors.

13 Claims, 17 Drawing Figures

MODULAR MULTI-TUBE CATALYST LOADING FUNNEL

This is a division of application Ser. No. 588,985, filed Mar. 13, 1984, now abandoned.

FIELD OF THE INVENTION

This invention relates to an apparatus and a process for loading catalysts into multi-tube reactors quickly and with maximum control over the catalyst drop rate and consequently control over the packed density of the catalyst in the reactor tubes. The invention is particularly applicable to jacketed multi-tube reactors used in the production of ethylene oxide, phthalic anhydride and maleic anhydride, but is not limited to such uses.

BACKGROUND OF THE INVENTION

Each of the reactions for producing ethylene oxide or the production of phthalic anhydride or maleic anhydride is highly exothermic, involving the controlled oxidation of organic substances. It is thus necessary that the heat generated by the reaction be removed as efficiently as possible so as to prevent a run-away reaction in which undesirable products are produced and in which expensive raw materials are wasted. Accordingly, it has been the practice to utilize catalytic tubes of extremely narrow diameter. Thus, for example, it is not unusual for a catalyst tube to have an ID of 1.25 inches and to be 60 feet in length. The reactor, however, may contain as many as 2,500 to 9,000 tubes. In one instance, for example, the reactor had tubes which were only 22 feet high, but each tube had an ID of $\mu$ of an inch and the reactor contained 8,600 tubes. Each of the tubes are rolled or otherwise joined at each end to a tube sheet and the entire bundle of tubes and the tube sheet is jacketed and filled with a heat transfer medium, as for example, Dowtherm TM, mercury, or molten salt solutions. Due to the heat given off by the reaction, the space velocity is maintained at an extremely high rate so that there is considerable abrasion of the catalytic spheres within the small diameter tubes. In order to maintain optimum selectivity, it is essential that the temperature be maintained within a relatively narrow range. Thus, as is pointed out by one patentee, in the case of the oxidation of ethylene to ethylene oxide, the optimum temperature for the reaction is in the range of 225° C. to 250° C. If the temperature falls below 225° C., the conversion rate is insufficient to be economically feasible. If the temperature goes above 250° C., the selectivity of the reaction for ethylene oxide decreases significantly with the concommitant loss of desired end product.

Generally speaking, it has been the practice to increase the temperature of the reaction as the activity of the catalyst begins to fade. However, as pointed out above, this has limitations, since once the temperature is increased above a certain limit, there is sufficient loss of selectivity to make the process economically unfeasible. It then becomes necessary to unload the catalyst and reload with new catalyst. Due to the high capital investment, it is essential that down time be maintained to a minimum. In most instances, turn-around time should be within less than five days.

DESCRIPTION OF THE PRIOR ART

Once the catalyst has been unloaded, the normal procedure is to sandblast the tubes to remove any vestiges of rust or of carbonaceous deposits on the walls of the tubes. Since, in sandblasting the tubes, some of the metal is removed, the surface becoming quite reactive, it is necessary to maintain the atmosphere at a very low humidity. In many instances, the tube sheets and the tubes are heated, the tubes purged with dry nitrogen, prior to beginning the loading operation. The loading operation is critical in that it is necessary to maintain the packed density of the catalyst within certain limits and to maintain the pressure drop across the bed, i.e. across each tube, within a very narrow range. The practice, therefore, has been, after sandblasting and purging of the tubes with dry nitrogen or dry air, to cap the tubes and to cover the exposed areas from the elements, in case of rain. The rate of catalyst drop is dictated through experience by the catalyst manufacturer to produce a packed density in the tubes sufficient to maintain an identical pressure drop in each of the tubes. For many years, the preferred catalyst shape had been in the form of Alundum spheres or Carborundum spheres (alpha alumina) onto which the catalytic material had been impregnated. In recent years, however, in order to improve the diffusion rate of the gases within the tubes, various other shapes have been introduced and these new shapes add further problems to the catalyst drop rate and to the method of catalyst loading. The most prevalent method of loading catalysts is a single funnel containing a single speed motor for rotating the metering rod. The only method of controlling the rate of catalyst drop in this instance, therefore, is to change the configuration of the metering rod or to raise or lower the metering rod in the mouth of the funnel. Certain vibrating feeders have been proposed and utilized, which consist essentially of a large plate containing as many as 3,500 holes registering with the tubes of a multi-tube reactor. This plate is vibrated by a large vibrator. The catalyst is poured onto the plate and the plate is vibrated to fill all 3,500 tubes, hopefully at the same catalyst drop rate and at the same time. This apparatus, of course, is large and bulky and requires removal of the upper portion of the reactor to allow access of the plate to the tube sheet.

SUMMARY OF THE INVENTION

According to this invention, a modular multi-tube funnel is provided in which each funnel module contains a hopper in which a rotatable metering rod is mounted. Each of the metering rods is heighth adjustable, so that the end of the metering rod can be raised or lowered in the mouth of the funnel to either increase or decrease the catalyst drop rate. Additionally, each of the metering rods is driven by a single motor, having a variable-speed speed reducer, so that the speed of rotation of all of the metering rods can be decreased or increased as desired. Thus, once the metering rods have been set, it is possible to vary the catalyst drop rate without the tedious heighth adjustment of the metering rods by variably adjusting the speed of rotation of the metering rods.

DESCRIPTION OF THE PREFERRED EMBODIMENT

As previously mentioned, this invention finds its application in processes involving the partial oxidation of ethylene to ethylene oxide, the partial oxidation of naphthalene or other organic material to phthalic anhydride and the partial oxidation of benzene or other organic materials to maleic anhydride. Due to the extreme exothermic nature of these reactions, it has been the practice to confine the gases and the catalyst in tubes of extremely small diameter but of considerable length. The tubes are surrounded by a heat transfer medium so as to maintain a method of absorbing the extreme heat produced by the reaction. As previously mentioned, the ID of the tubes runs in the range of from 2.0 inches to less than ¾ of an inch and the length of the tubes range from 10 feet to 60 feet. Some reactors will contain 2,500 tubes, while some of the even larger reactors will contain more than 20,000 of the small-diameter tubes. The capital investment required for precision engineering tube sheets for securing the tubes in the jacketed reactors and for the controls essential to maintain the temperature of the reaction within a specified narrow range, is quite substantial. As a consequence, when it becomes necessary to change out the catalyst, turn-around time or down time must, of necessity, be kept to as small a time as possible. Normally, this is less than five days. During that time, it is necessary to first unload the catalyst, in which some of the catalyst has bridged across the tubes and formed carbonaceous deposits and this procedure is accomplished by the use of "fish tapes" of 50 or 60 feet in length, which are inserted into the tubes so as to break loose any carbonaceous material or burnt catalyst which has bridged across the tubes during the reaction. Normally, it is expected that this procedure be carried out at a rate of at least 50 tubes per hour. The work is so difficult that one major producer specifies that the workmen work in one-hour shifts and rest for one hour so as to maintain maximum efficiency. Thereafter, it is necessary to sandblast the tubes to remove any traces of rust or carbonaceous deposits that might remain after the unloading. Once this has been accomplished and all of the excess sand cleaned up so as not to possibly get into the tubes, the tubes are purged, generally with a hot, dry nitrogen purge or, in some cases, the tube sheet and the tubes are heated up to a temperature sufficiently high to prevent any moisture from settling on the tube's raw surface. Thereafter, the tubes are capped or otherwise protected awaiting the catalytic loading procedure.

The loading procedure normally requires a particular catalyst drop rate in the tube. This drop rate has been established empirically by the producer or by the catalyst manufacturer as being sufficient to equally load each of the tubes so that one or more tubes does not have a substantially higher pressure drop than the others. In one of the major producer's steps for production, once the tubes have been capped, the inerts are loaded at the bottom of the tube by two men. This is accomplished by pouring a quart of the large-diameter alpha alumina spheres into each tube so that the distance between the outlet of the tube sheet to the top of the tube sheet is filled with noncatalytic material. It is essential that no reaction occurs in the areas of the tubes occupied by the heat transfer media. Otherwise excess heat will cause carbonaceous deposits and catalyst bridging, thus taking the tube out of service. Therefore, sufficient inerts are added so that the area of the tube surrounded by the tube sheet does not contain active catalytic material. Normally, the tube sheets are from 6 to 13 inches in thickness. Therefore, enough inert spheres are added to insure a tube depth equal to or in excess of the tube sheet thickness. The major requirement is that the same amount of inert spheres is added to each tube so as to produce an equal pressure drop. In the past, this operation has required two men. One man uncaps the tubes while the other fills a quart or liter container. The inert spheres are poured into the tube and the tube is recapped while the other man is filling another container for the next tube.

Once this has been done for all 20,000 tubes, which involves uncapping, pouring in the inert spheres and recapping the tubes, the loading procedure can be begun. As previously indicated, the preferred catalyst drop rates have been established and become part of the specifications. According, now, to the present invention, one man, having tested the catalyst drop rate of his modular funnel, in a drum or other receptacle, so that it is within specifications, can load eight tubes in one operation. Additionally, it is possible for one man to uncap eight tubes, pour a quart of the inert noncatalytic spheres into the hopper and feed them into the bottom of each of the tubes; thereafter, load each of the hoppers with the proper amount of catalyst and rotate all eight metering rods at the same identical speed to establish a controlled catalyst drop rate. Thereafter, the operator merely moves the entire assembly of eight tubular spouts to another eight tubes and again loads these with inerts, followed by loading same with the catalyst at the proper drop rate. While the catalyst is being loaded, the operator can measure the "outage" which is the distance from the top of the tube sheet to the level of catalyst. He then records the "outage" either through colored caps or by writing onto the caps the "outage"

measurement. In some procedures, he indicates by different colored caps whether the "outage" is within specifications or is an over-fill or an under-fill.

Once all the tubes have been filled and capped, the dust is blown down through the tube to the bottom of the reactor. A vacuum truck connected at the bottom of the reactor can draw any dust "blown down" away.

Thereafter, the "outage" is adjusted within specifications by manually vacuuming off additional catalysts past a certain limit (at least below the bottom of the tube sheet). In other instances, some catalyst may be added to compensate for under-fill, again within set limits.

Thereafter, each tube is tested for pressure drop ($\Delta P$). If any tube fills outside of the specified limits, and cannot be brought into specification by addition or subtraction of catalyst from the tube, the tube must be unloaded and refilled. Since the number of tubes run into the thousands, these various measurements and adjustments are time consuming. Nevertheless, a tube with a high pressure drop will not allow the proper flow of gases through it so that its effectiveness is lost. A tube with a low pressure drop will allow too much gas to pass through it, resulting in quick deactivation of that catalyst tube and loss of selectivity for that portion of the reactor. The goal is to have a uniform packed density and a uniform $\Delta P$ in each of the tubes. This is accomplished by a uniform catalyst drop rate for all the tubes in the reactor.

Figure 1:
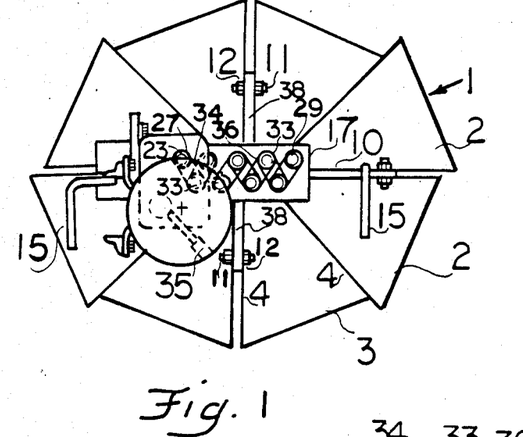
FIG. 1 is a plan view of the modular multi-tube loading funnel of this invention.
Figures 2, 3:
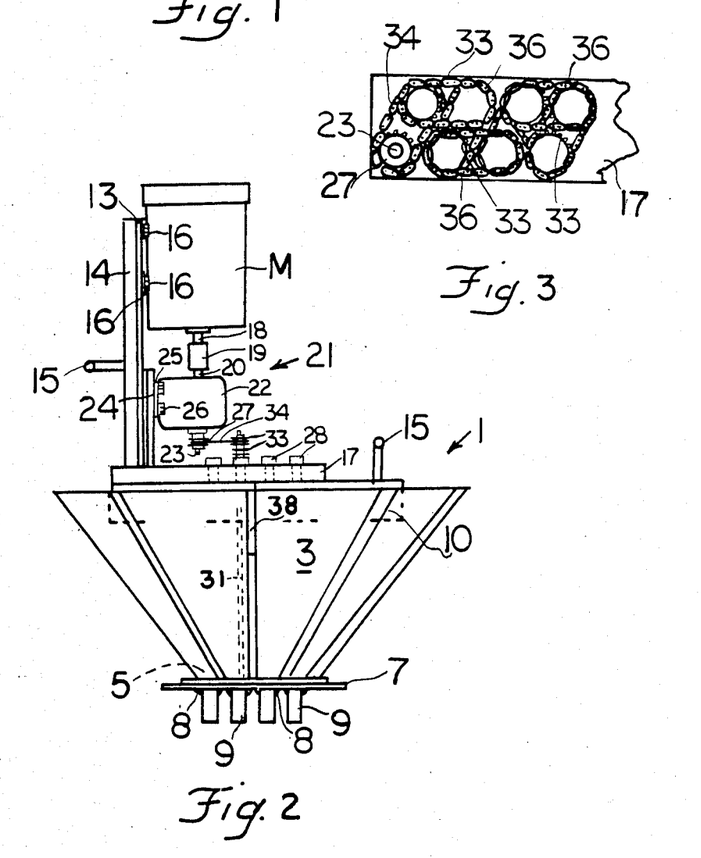
FIG. 2 is a side elevation of the loading funnel shown in FIG. 1.
FIG. 3 is a view of the sprocket and chain drive of the modular funnel shown in FIGS. 1 and 2.

Referring more closely to the drawings, the modular multi-tube funnel 1 is shown in FIGS. 1–3 as being made up of eight funnel modules or hoppers 2. In the configuration shown, the funnel modules are pyramidal in shape, having an end wall 3 and two side walls 4, joined together, with an outlet 5 (not shown) at the bottom of the truncated pyramid. It is, of course, within the scope of this invention to use other shapes, such as rectangular hoppers and I do not wish to be bound to the pyramidal shape of a funnel module illustrated herewith. A centering plate 7 is welded to the modules through welds 8, and tubes 9 are welded to the holes in the centering plate, which are in registry with the outlets 5 from the hoppers 2.

A median plate 10 acts as a support for the modules 2 and this, in turn, is joined with a support plate 38 which runs more or less transversely at 90° from the median plate 10. The median plate is bolted by means of bolt 11 and fastened by nut 12 to the walls 4 of the funnel modules 2. Handle 15 is connected to the median plate 10 and another handle 15 is connected to the vertical angle iron 14 so as to allow the operator to move the modular multi-tube funnel from location to location. The motor M is mounted by means of a motor mounting 13 by means of bolts 16 and washers to the vertical angle iron 14. The motor M has a drive shaft 18 which is connected via coupling 19 to driven shaft 20 of the speed reducer 21, consisting of the gear box 22 which has a drive shaft 23 at its opposite end. The gear box 22 is mounted to mounting bracket 25 and vertical angle iron 24 by means of bolts 26. The speed reducer has a lever 35, shown in phantom lines in FIG. 1, whereby the speed of the drive shaft 23 from the gear box can be variably adjusted. Mounted on the drive shaft is a drive sprocket 27 which is joined to the driven sprockets 33 mounted on the machined hollow shafts 29 journalled in the flanged bushings 28 of the shaft support plate 17. As can be seen clearly in FIG. 2, the drive shaft 23 drives the drive sprocket 27 by means of chain 34 trained over driven sprockets 33. Each of the machined shafts 29 are journalled in flange bushings 28 mounted in the shaft support plate 17. Each of the shafts 29 in the modification shown in FIG. 2 and in FIG. 3 contains two sprockets: one at a lower level, around which driven chains 36 are train in pairs. In this method, each of the metering rods 31, which are fitted into the hollow machine shaft 29 and held in place by pin 30 and set screw 32 are driven at the same speed of rotation. It is, of course, possible to change the catalyst drop rate by changing the location of the end of the metering rod 31 in the mouth of the funnel, however, once the metering rods have been set, it is still possible to change the drop rate by merely changing the speed of rotation of the metering rods through manipulation of lever 35.

Figure 4:
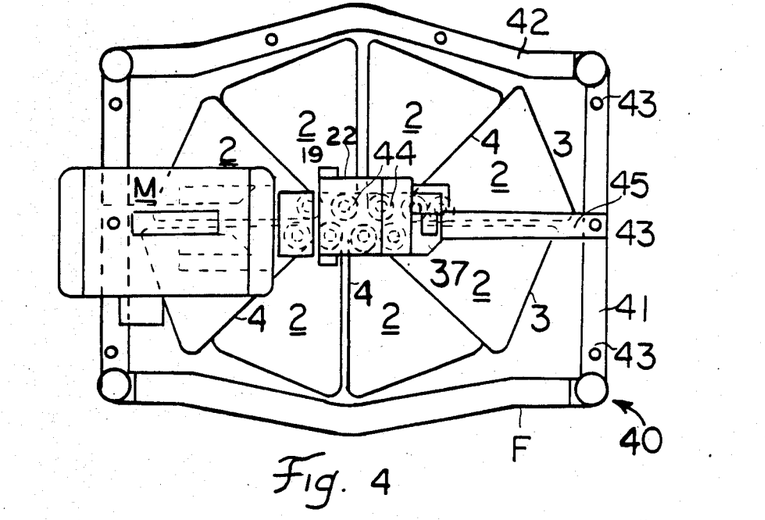
FIG. 4 is a plan view of another modification of the loading funnel, supported on an adjustable carriage.

While the drive mechanism for the speed reducer has been shown to be a sprocket and a series of chains connecting pairs of sprockets, it is possible to use a single serpentine chain, turning all eight of the sprockets simultaneously and at the same speed or to use a gear-driven mechanism. A gear drive is illustrated in FIG. 4, in the modification shown in which the drive assembly, including the motor M, the coupling 19, the gear box 22 and the right angle drive 37 is utilized with the drive assembly located horizontally rather than vertically on an adjustable carriage 40 to reduce the amount of headroom required. In this case, the drive shaft 23 powers a drive gear, which is meshed with gears 44 and with idler gears (not shown) so that all of the gears are driven at the same speed as the drive shaft 23. This, again, is controlled by the lever 35.

Figure 5:
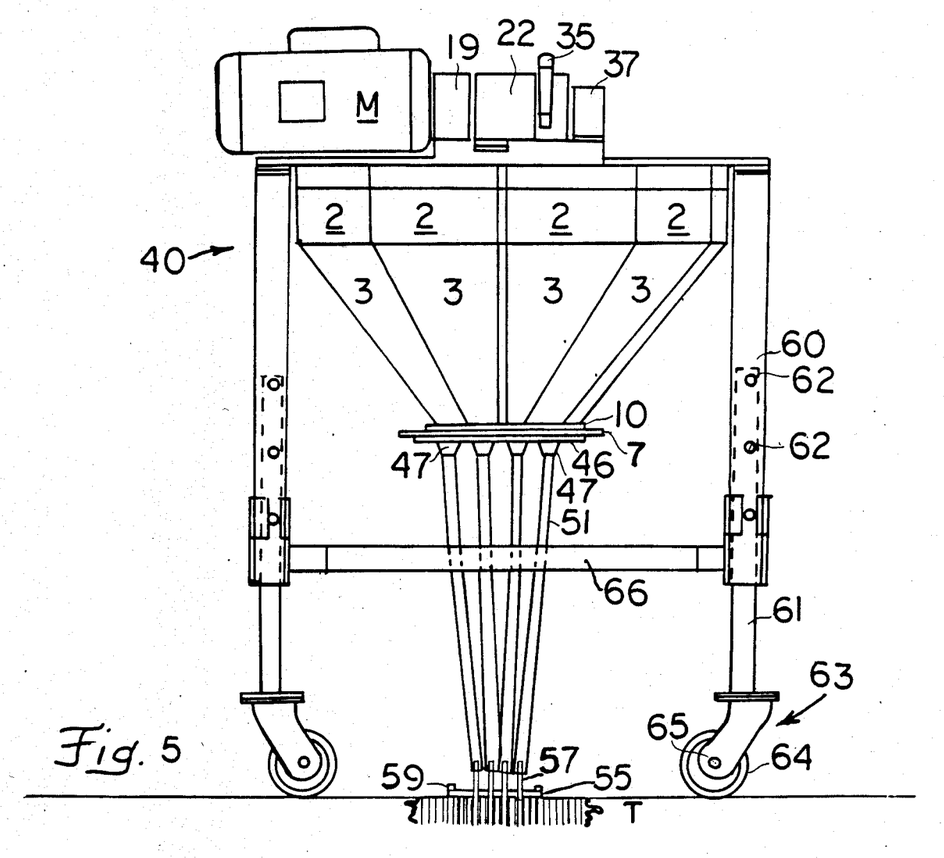
FIG. 5 is a side elevation of the loading funnel and adjustable carriage illustrated in FIG. 4.
Figure 6:
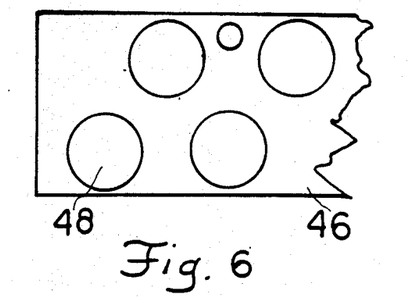
FIG. 6 is a fragmentary plan view of the transitional tube plate of the modular multi-tube loading funnel shown in FIGS. 4 and 5.

The drive assembly, however, is supported on a support plate 45, spanning the frame F, consisting of two side members 42 and two end members 41 in which the end members contain bolt holes 43 to register with bolt holes in the support plate 45. As will be seen in FIG. 5, the legs 60 of the adjustable carriage contain telescopic members 61 and holes 62 so that the height can be adjusted by removal or insertion of pins through the proper hole. Additionally, the end of the telescopic portion of the legs 61 is fitted with a wheel assembly 63, having a bifurcated fork in which the wheel 64 is journalled in axle 65. In this modification, the centering plate 7 merely surrounds the bottom of the hoppers 3 and the transition plate 46 is used to funnel the catalyst pellets into the funnel endpieces 47 and into the tubes 49. The dimensions of the bell housings, which are used to form the funnel portion 47 of the funnel member are identical to the diameter of the holes 48 of the transition plate 46 and the bell housing or funnel member 47 is welded into place by weld 50 and the tubular member is welded onto the end of the bell housing 47 by weld 50. The metal tubular member is then fitted with flexible tubes 51 made of Tygon TM inserted over said tubes 49 and metal spouts 57 which are essentially of the same diameter as the tubes of the tube sheet T to be loaded.

Figure 7:
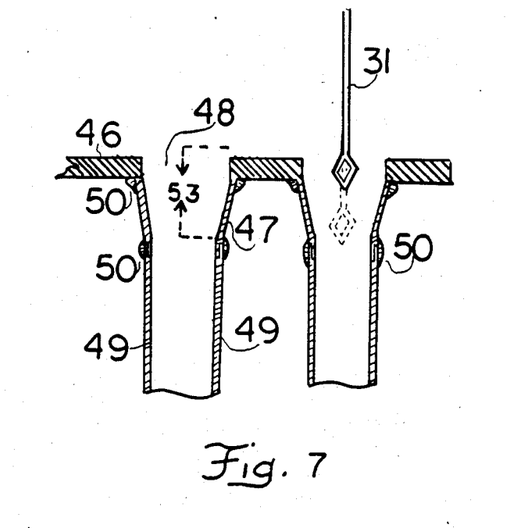
FIG. 7 is a fragmentary sectional view of the transitional tube plate.

The transition zone 53 is essentially the area slightly above the top of the transition plate 46 down into the mouth of the funnel member as is shown in phantom lines in FIG. 7. Generally speaking, the drop rate of the catalyst can be decreased by lowering the end of the metering rod 31 to the position shown in FIG. 7 in phantom lines and can be increased by raising it to the level shown in full lines.

Figure 8:
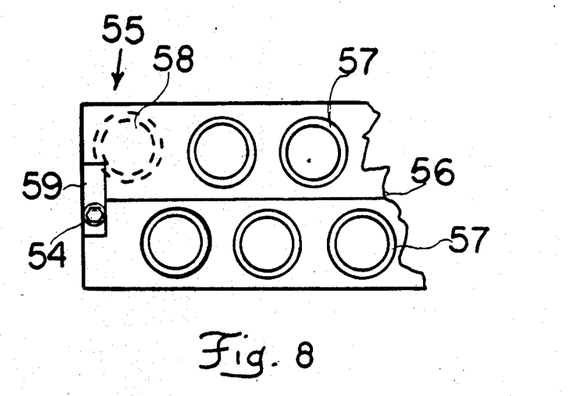
FIG. 8 is a fragmentary plan view of the tube locating base plate of the modular multi-tube loading funnel illustrated in FIGS. 4, 5 and 6.
Figure 9:
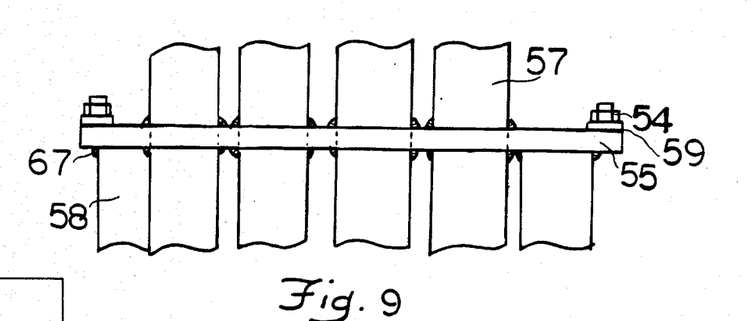
FIG. 9 is a fragmentary side view of the tube loading base plate.

It should be noted that by use of the transitional tube plate 46, it is not essential that the openings be on center with the centers of the tubes to be loaded. This is accomplished by means of the tube locating base plate 55, illustrated in FIGS. 8 and 9. As is shown, the tubes 57 of the tube locating base plate 55 are on center with the tubes in the tube sheet T of the reactor to be loaded and are equipped with tubular spouts 57 welded into position by welds 67. A tubular guide pin 58 of essentially the same diameter as the tubes to be loaded and which depends from either end of the tube locating base plate 55, is used as a stabilizing means to maintain the eight tubular spouts 52 properly located in the tubes of the tube plate T. The tubular guide pin or projection 58 is welded to the bottom of tube locating base plate 55 by weld 67.

As will be noted, the tube locating base plate 55 is split along its center axis at point 56 and is held together by means of a strap 59 welded to one half and bolted by bolt 54 to the other half. The reason for this will become clear upon review of FIG. 10, in which it is shown that half of the funnel modules 2 have been removed from the modular funnel 1 and the support plate 45 has been moved from the middle of the adjustable carriage 40 to the far edge of the rectangular frame F and pinned into position by registry of the bolt holes in the support plate 45 and the holes 43 of frame member 41. This is to allow for loading of the tubes close to the circumference of the circular reactor wall R. By this method, the tube locating base plate 55 can be merely separated along the split 56 by removal of bolt 54 along with the four tubular spouts 52 associated therewith and the four hoppers or funnel modules so that only four units are available to load the tubes at the far edge of the circumference of the reactor. After these tubes, which are generally inaccessible, are loaded, the four modules can be placed back onto the assembly and the spanning plate 45 moved to the middle of the carriage frame F.

Figure 10:
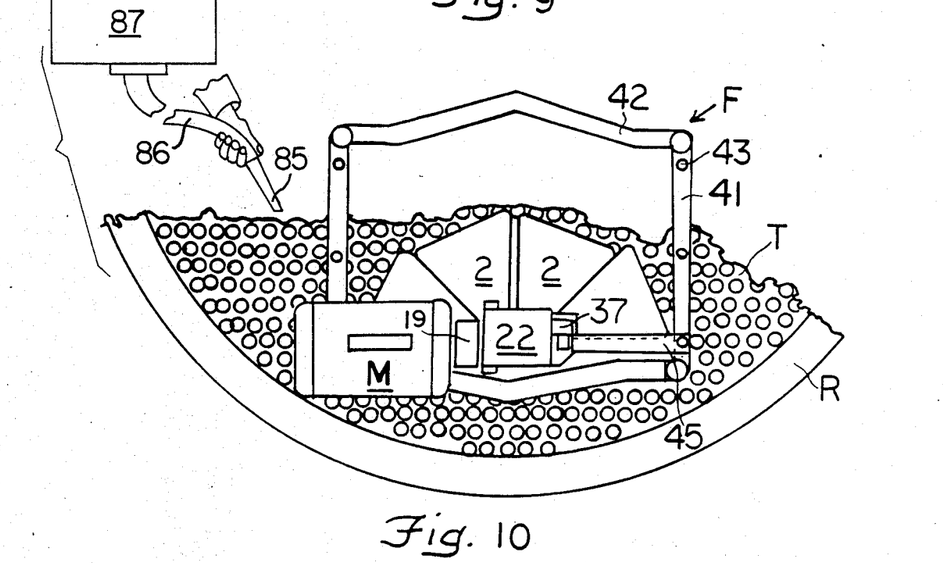
FIG. 10 is a plan view of the adjustable carriage with one half of the funnel modules removed and the remaining modules and drive assembly moved to the far side of the carriage.

Additionally, a vacuuming hose 85 is shown in FIG. 10, having a nozzle 86 for removing excess catalyst from the tubes of the reactor. This is done manually after it is determined by manual measurement that an overfill exists. As previously mentioned, it is essential that the catalyst level be below the lower level (at the top) or the upper level (at the bottom) of the tube sheet. Hose 85 is attached to a vacuum source 86, for drawing excess catalyst out of the reactor tubes so that the catalyst level does not extend into the area of the tube sheet.

Figure 11:
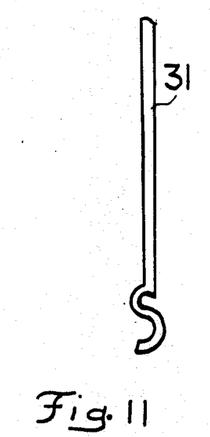
FIG. 11 is a side elevation of a metering rod having a terminal portion in the shape of an S.
Figure 12:
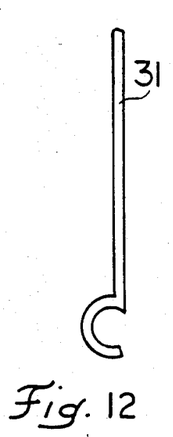
FIG. 12 is a side elevation of a metering rod having a terminal portion in the shape of a C.
Figure 13:
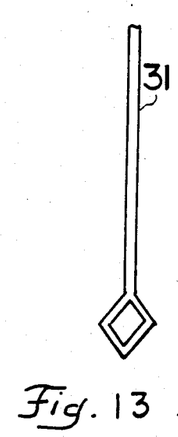
FIG. 13 is a side elevation of a metering rod having a terminal portion in the shape of a diamond.
Figure 14:
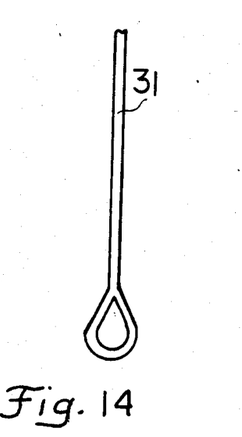
FIG. 14 is a side elevation of a metering rod in the shape of a loop.

FIGS. 11 through 14 show different configurations which can be used with the apparatus of this invention, as well as the straight metering rod 31. In FIG. 11, the terminal end is in the shape of an S and in FIG. 12, the end of the metering rod 31 is in the shape of a C. In FIG. 13, the end of the metering rod is in the shape of a diamond and in FIG. 14, the end of the rod is in the shape of a loop. Other configurations are useful. It is essential, however, that the same configuration be used in each hopper and that the length or the relation of the end of the metering rod 31 to the mouth of the funnel 47 in the transition zone 53 be the same in all cases.

Figure 15:
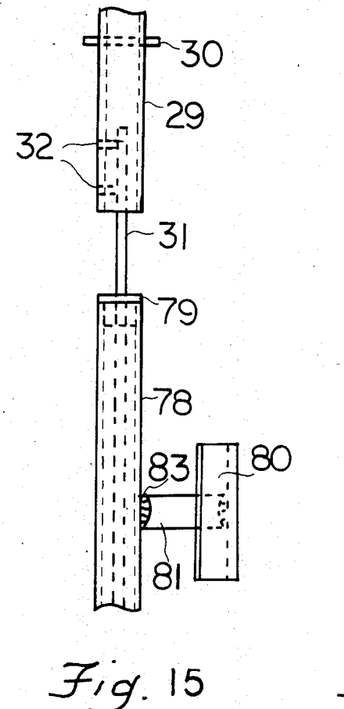
FIG. 15 is a side elevation of a protective tube for the shank of a metering rod.

FIG. 15 illustrates a protective tube 78 for the shank of metering rod 31. The protective tube 78 is fitted with a brass bushing 79 at each end for journaling of the shaft of metering rod 31. The tube is then crimped over the bushing 79 to hold it in place. A bracket 80 is attached to the wall 4 of the hopper 2 by suitable means, such as welding. The bracket 80 is, in turn, attached to a supporting arm, which in turn, is connected to the protective tube by weld 83. Another bracket 80 and supporting arm 81 is preferably used at the bottom of the protective tube 78.

FIG. 15 also illustrates the end of the metering rod 31, mounted in the machined hollow shaft 29 and held in position by set screws 32 and by transverse pin 30.

The protective tube 78 protects the shank of the metering rod 31 from the abrasive action of the alpha alumina, normally used as a catalyst carrier.

Figure 16:
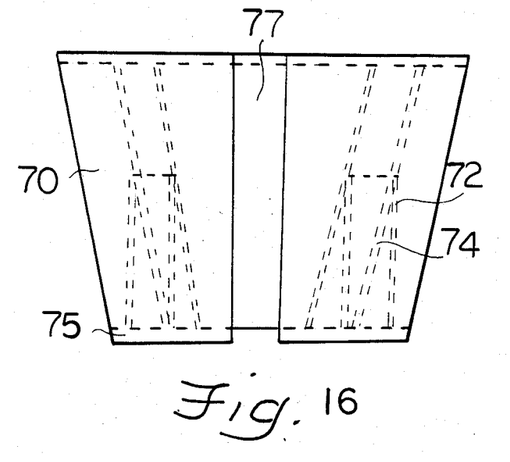
FIG. 16 is a front view of a bag support hopper extension and FIG. 17 is a side view of a bag support hopper extension.
Figure 17:
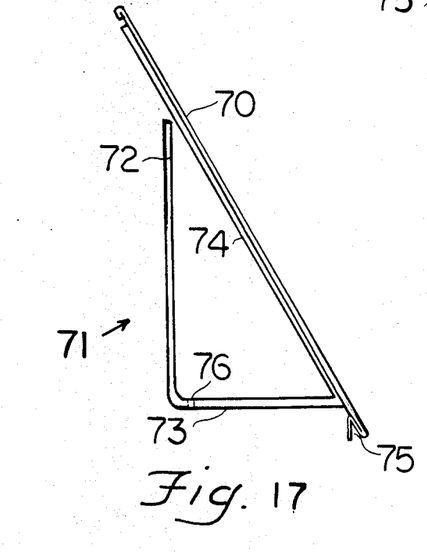

Another accessory which can be used in conjunction with the apparatus of this invention is a bag support plate 70, supported on a bracket 71 in the shape of a triangle. The triangular bracket 71 has a vertical support 72, a base portion 73 and an inclined support 74, which is equivalent to the hypotenuse of the triangle on which the support plate 70 is attached. The bottom of the bag support plate 70 is bent into an inverted V-shaped clip 75 to fit on the wall of hopper 2. The base of the support bracket can then be attached to the frame of the adjustable carriage by clamps or through bolt holes or other means known in the art. In FIG. 16, the support plate 70 is joined to another support plate by connecting piece 77 bent so as to conform with the side member 42 of frame F.

Many modifications will occur to those skilled in the art from the detailed description hereinabove given, which is meant to be exemplary in nature and nonlimiting except so as to be commensurate in scope with the appended claims.

I claim:

1. A process for the simultaneous loading of a plurality of tubes of a catalytic reactor at a uniform catalyst drop rate, utilizing a multi-tube catalyst loading funnel, equipped with a plurality of hoppers, with tubular outlets, each hopper having a rotatable metering rod mounted therein, which comprises the steps of:
   A. adjusting the length of the metering rod so as to be identical for each of the hoppers;
   B. adjusting the speed of rotation of the metering rods so as to be identical for each of the hoppers,
   C. inserting the tubes from said multi-tube hopper into the tubes of the catalytic reactor to be loaded;
   D. adding a given volume of catalyst pellets to each of the hoppers;
   E. controlling the catalyst drop rate of the catalyst pellets into the tubes of the reactor;
   F. moving the multi-tube funnel and tubes to an adjacent set of tubes in the reactor;
   G. filling each of the hoppers with a given amount of catalyst and repeating the fill operation;
   H. measuring the depth of fill of the filled tubes;
   I. capping the filled tubes.

2. A process for loading reactor tubes, as defined in claim 1, the improvement of:
   A. decreasing the drop rate of the catalyst pellets by increasing the length of the metering rod in the hopper.

3. The process for loading reactor tubes, as defined in claim 1, the improvement of:
   A. decreasing the drop rate of the catalyst pellets by decreasing the speed of revolution of the metering rods.

4. A process for loading reactor tubes, as defined in claim 1, the improvement of:
   A. increasing the drop rate of the catalyst pellets by shortening the length of the metering rod in the hopper.

5. A process for loading reactor tubes, as defined in claim 1, the improvement of:

A. increasing the drop rate of the catalyst pellets by increasing the speed of rotation of the metering rod.

6. A process for loading reactor tubes, as defined in claim 1, the improvement of changing the drop rate of the catalyst pellets by changing the configuration of the metering rods in the hoppers.

7. The process for loading reactor tubes, as defined in claim 1, the improvement of vacuuming tubes with an over-fill to a level equal with the thickness of the tube sheet of the reactor and thereafter recapping with a colored cap, indicating proper fill.

8. A process for loading reactor tubes, as defined in claim 1, the improvement of uncapping tubes with an under-fill and adding catalyst thereto to a level equal with the bottom of the tube sheet of the reactor, and then recapping with a colored cap, indicating proper fill.

9. A process for loading reactor tubes, as defined in claim 1, the improvement of unloading tubes not meeting specifications from the bottom and subsequently refilling with catalyst pellets to meet specification.

10. A process for loading reactor tubes, as defined in claim 1, which includes the steps of:
   A. uncapping the unfilled tubes prior to filling; and
   B. thereafter recapping the filled tubes with caps of a different color.

11. A process for loading reactor tubes, as defined in claim 1, which comprises the steps of
   A. pouring a given quantity of inert catalyst carriers equivalent to a tube depth equal to the thickness of the tube sheet into each of the hoppers and loading said inert carriers in the tubes of the reactor prior to loading of the catalyst pellets into said hoppers.

12. A process for loading reactor tubes, as defined in claim 1, in which said multi-tube catalyst funnel is supported on an adjustable carriage and in which said funnel has a series of flexible tubes depending from said tubular outlets, the step of loading the tubes close to the periphery of said catalytic reactor which includes:
   A. removing half of the funnel hoppers from the modular funnel;
   B. moving the remaining half of said funnel hoppers to the far edge of the adjustable carriage: and
   C. inserting the flexible tubes into the reactor tubes at the periphery of the catalytic reactor.

13. A process for loading reactor tubes, as defined in claim 12, in which said modular multi-tube funnel is equipped with a tube locating base plate, split along its long axis into halves and having holes in each half with centers registering with the centers of the reactor tubes,
   A. the step of separating said base plate and the flexible tubes connected therewith when removing half of the funnel hoppers from the modular funnel.

* * * * *